United States Patent [19]
Appavu

[11] Patent Number: 6,019,187
[45] Date of Patent: Feb. 1, 2000

[54] DISPOSABLE STETHOSCOPE COVER DIAPHRAGM

[76] Inventor: Aramudhan S. Appavu, 1926 W. Harrison St. 1716, Chicago, Ill. 60612

[21] Appl. No.: 09/039,174

[22] Filed: Mar. 13, 1998

[51] Int. Cl.[7] .................................................. A61B 7/02
[52] U.S. Cl. ................................................ 181/131
[58] Field of Search .................... 181/131, 137; 381/67

[56] References Cited

U.S. PATENT DOCUMENTS

| | | |
|---|---|---|
| 3,255,841 | 6/1966 | Hasbrouck . |
| 4,461,368 | 7/1984 | Plourde . |
| 4,867,268 | 9/1989 | Ulert ............................. 181/137 |
| 5,269,314 | 12/1993 | Kendall . |
| 5,365,023 | 11/1994 | Lawton . |
| 5,428,193 | 6/1995 | Mandiberg . |
| 5,466,897 | 11/1995 | Ross et al. ...................... 181/131 |
| 5,686,706 | 11/1997 | Wurzburger . |

*Primary Examiner*—Khanh Dang
*Attorney, Agent, or Firm*—Don Moyer

[57] ABSTRACT

A cover diaphragm is removably attached over the outer edge of a stethoscope high frequency pickup in order to isolate the pickup from pathogens contacted when the stethoscope is used to examine a person. The cover diaphragm can be used as the diaphragm of a stethoscope high frequency pickup and can be used with a diaphragm supplied with the stethoscope. After the cover diaphragm has been used it can be discarded and destroyed by known safe procedures and alternatively can be cleaned by known safe procedures for reuse.

4 Claims, 2 Drawing Sheets

DISPOSABLE STETHOSCOPE COVER DIAPHRAGM

BACKGROUND OF THE INVENTION

The invention is a cover diaphragm which easily attaches around the outer edge of a stethoscope pickup, which is the only part which will contact a person examined with the stethoscope, which is disposable, which can be cleaned for reuse, which can be used in place of a diaphragm supplied with the stethoscope, and which can be used with a supplied diaphragm.

When parts of a stethoscope contact a person being examined by the stethoscope these contacting parts become contaminated with any pathogens contacted on the person, and then when this stethoscope is used to examine another person those pathogens are transmitted to the second person. This problem has been acknowledged in prior art where several solutions have been shown. These solutions however do not keep the acoustic properties of the stethoscope constant from one use to the next, do not have the features of this cover diaphragm, and can not be used alone as the diaphragm for a stethoscope high frequency pickup.

In U.S. Pat. No. 3,255,841 Hasbrouck shows a cover for a bell stethoscope pickup. The bell pickup is used for listening to low frequency sounds whereas a diaphragm pickup is used for listening to high frequency sounds. The diaphragm attenuates low frequency sounds to make the high frequency sounds easier to hear. The Hasbrouck cover can not be used with a supplied diaphragm because of its shape and can not be used in place of a supplied diaphragm because it does not have the low frequency attenuating property needed for a diaphragm pickup.

In U.S. Pat. No. 4,461,368 Plourde teaches an elastic cover for a diaphragm pickup. This can not be used in place of a supplied diaphragm because it has elasticity designed to conform to an examinee's skin and this skin conformable elastic cover does not have the stiffness needed to attenuate low frequency sounds. Also, the layer of air trapped between this cover and a supplied diaphragm will change the acoustic properties of the pickup. Unavoidable variations in the tension in this cover and in the pressure of the trapped air will change the acoustic properties of the stethoscope from one use to another. These limitations are shared by the skin conformable elastic sheath stethoscope covers shown in U.S. Pat. No. 5,269,314 by Kendall, in U.S. Pat. No. 5,365,023 by Lawton, and in U.S. Pat. No. 5,428,193 by Mandiberg.

In U.S. Pat. No. 5,686,706 Wurzburger shows an adhesive diaphragm cover which is attached onto a supplied diaphragm. This can not be used in place of the diaphragm onto which it must be attached. When it is used with the supplied diaphragm it will change the acoustic properties of the diaphragm pickup. Buildup of adhesive on the supplied diaphragm over time from using these covers will further change the acoustic properties of the diaphragm pickup from one use to another whereas generally constant acoustic properties are desired so that stethoscope users can appropriately evaluate the sounds heard.

The prior art suggestions do not solve the problem of isolating a stethoscope pickup from pathogens without introducing unwanted changes in the acoustic properties of the stethoscope.

SUMMARY OF THE INVENTION

Objects of this invention comprise requirements listed in the following imperatives. Make a cover for a stethoscope high frequency pickup which attaches around the outer edge of the pickup. Make the cover be the only part of the stethoscope which will contact a person being examined with the stethoscope. Make this cover disposable. Make this cover so that it can be cleaned and reused. Configure the cover and give the cover acoustic properties so that it can be used in place of a diaphragm supplied with the stethoscope. Configure the cover diaphragm so that stethoscopes can be devised together with the cover diaphragm in order to optimize the acoustic properties of the stethoscope and optimize the ease and reliability of attaching and removing the cover diaphragm. Configure the cover diaphragm and give the cover diaphragm acoustic properties so that the cover diaphragm can be used with the supplied diaphragm. Configure the cover diaphragm and give the cover diaphragm acoustic properties so that when replicas of the cover diaphragm are used one after another, then the acoustic properties of the stethoscope do not change from one use to the next. Make this cover diaphragm have low cost and be reliable, easy to manufacture, and easy to use.

Other objects will be comprehended in the drawings and detailed description, which will make additional objects obvious hereafter to persons skilled in the art.

In summary, one embodiment of this cover diaphragm has an outer band which encircles the outer edge of a high frequency pickup of a stethoscope, has an annulus attached to the outer band and extending over the outer edge to just beyond the inner edge of the pickup, has an inner band attached to the annulus and encircled by the outer band, and has a disc attached to the inner band, the disc attenuating low frequency sounds, the cover being the only contact with a person being examined with the stethoscope, and the cover isolating the stethoscope from pathogens.

Other equivalent embodiments will be comprehended in the drawings and detailed description, which will make additional equivalent embodiments obvious hereafter to persons skilled in the art.

DESCRIPTION OF THE PREFERRED EMBODIMENTS

Figure 1:
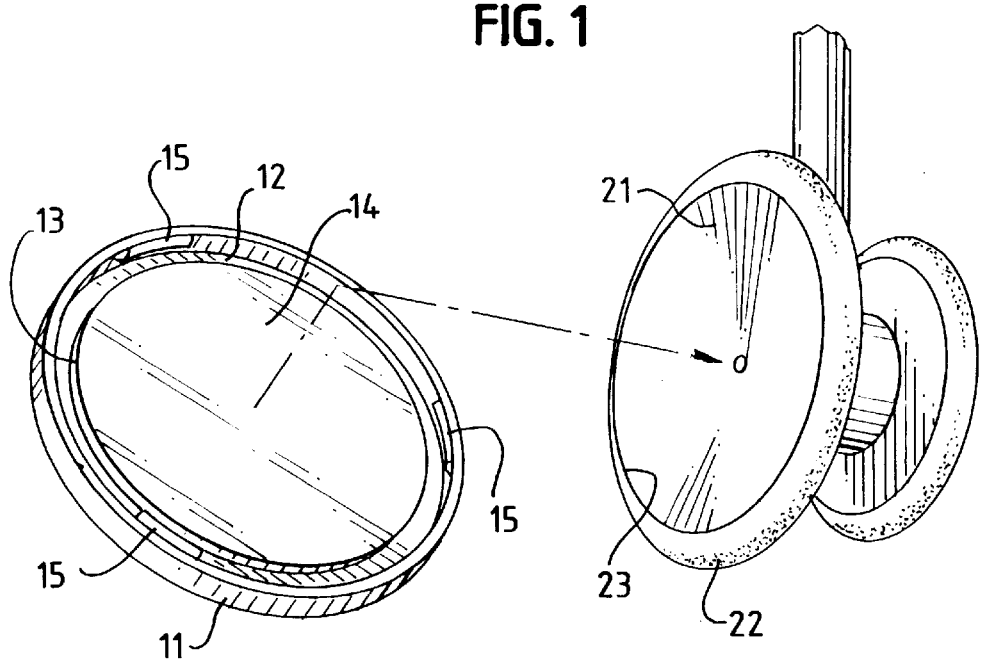
FIG. 1 shows the cover diaphragm and a stethoscope high frequency pickup.
Figure 2:
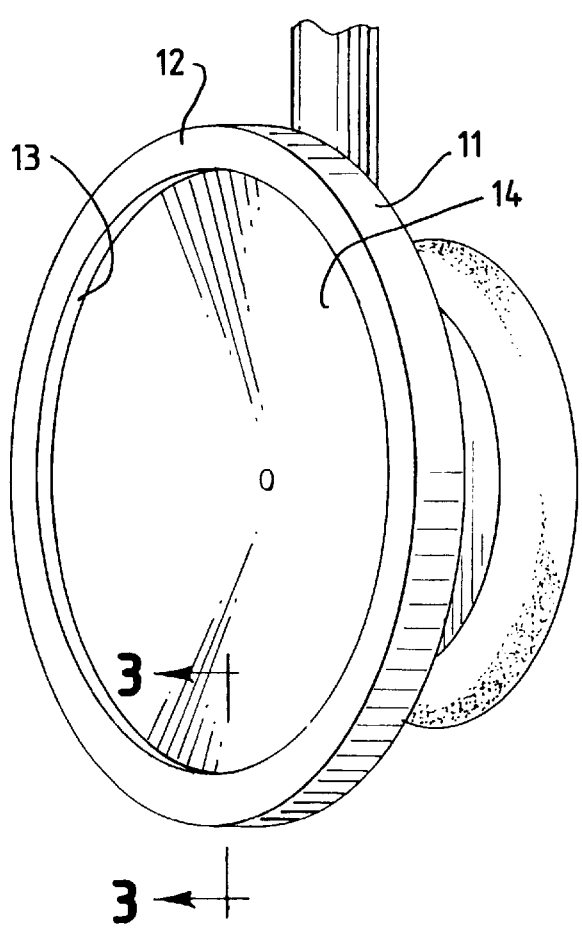
FIG. 2 shows the cover diaphragm on the pickup.
Figure 3:
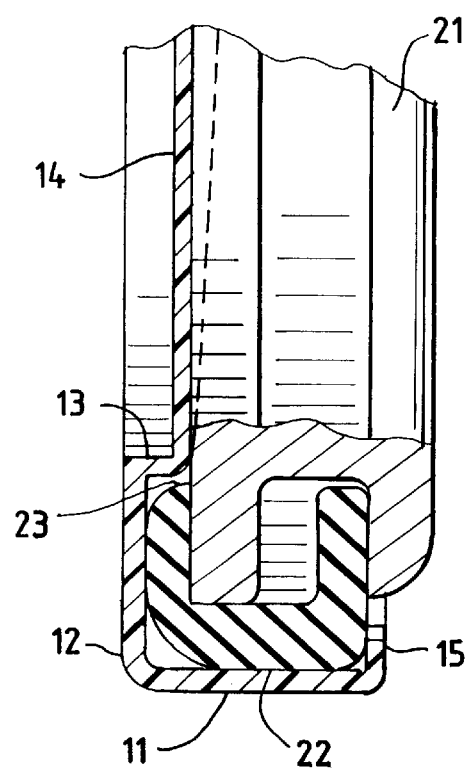
FIG. 3 shows a cross section of the cover diaphragm on the pickup.

The cover diaphragm is shown in FIG. 1 in position to be placed over a high-frequency pickup 21 of a stethoscope and is shown in place on the pickup in FIG. 2 and FIG. 3. The pickup is encircled by an inner edge 23, and the inner edge 23 is encircled by an outer edge 22. The cover diaphragm has an outer band 11 which encircles the outer edge 22 of the pickup, has an annulus 12 which is attached to the outer band 11 and which projects just past the pickup inner edge 23, has an inner band 13 which is attached to the annulus 12 and which is encircled by the outer band 11, and has a disc 14 which is attached to the inner band 13.

The cover diaphragm thus covers the pickup so that when the stethoscope is used to examine a person, then only the cover diaphragm touches the person and the pickup itself is isolated from contact with any pathogens which may be contacted by the cover diaphragm on touching the person. The used cover diaphragm is then removed from the pickup and replaced with a clean cover diaphragm. Thus any pathogens picked up by the used cover diaphragm are not transferred to another person examined with the stethoscope. A used diaphragm can be discarded and destroyed according to known safety procedures. A used diaphragm can also be cleaned to destroy and remove any pathogens according to known safety procedures so that this cleaned cover diaphragm can be used again.

The form of the cover diaphragm shown has three ears 15 located 120 degrees apart and each protruding inwardly toward the disc 14. As these ears pass over the pickup outer edge 22 this strains the outer band 11 outwardly. When the cover diaphragm is in place on the pickup, then these ears protrude inward under the pickup outer edge thus holding the cover diaphragm on the pickup. This makes attaching the cover diaphragm over the pickup especially easy and reliable. A cover diaphragm can be held on the pickup without these ears. When a cover diaphragm without these ears is placed over the pickup the outer band 11 of the cover diaphragm is strained outward slightly as it moves over the pickup outer edge 22 so that the cover diaphragm is held on the pickup outer edge 22 by the inward elastic force of the slightly strained outer band. Various forms of the outer band of the cover diaphragm with protruding ears as shown, with protruding rims and other protrusions, and without any protrusions can be attached easily and reliably over a stethoscope pickup.

Figure 4:
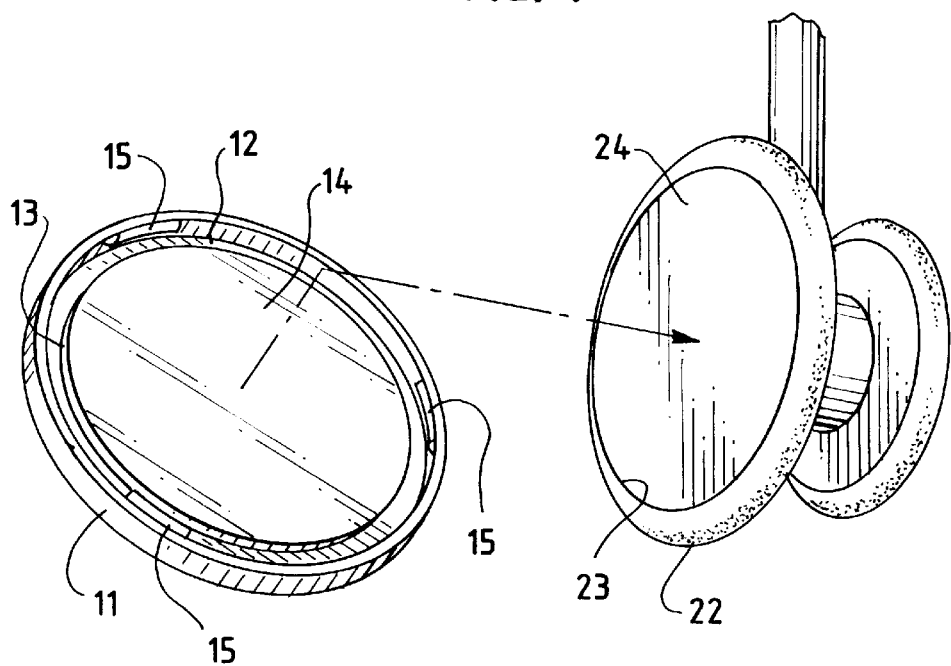
FIG. 4 shows the cover diaphragm and a stethoscope high frequency pickup with a diaphragm supplied with the pickup in place.
Figure 5:
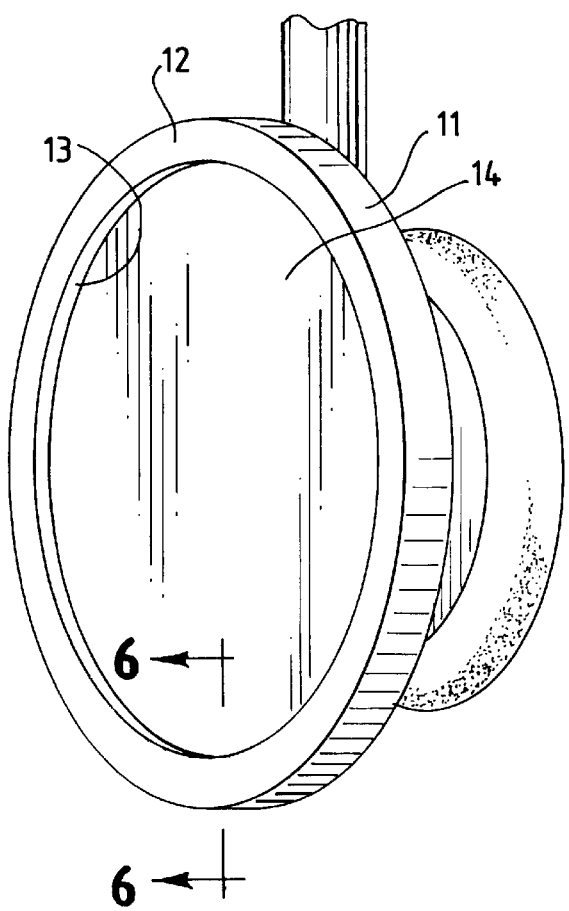
FIG. 5 shows the cover diaphragm on the pickup of FIG. 4.
Figure 6:
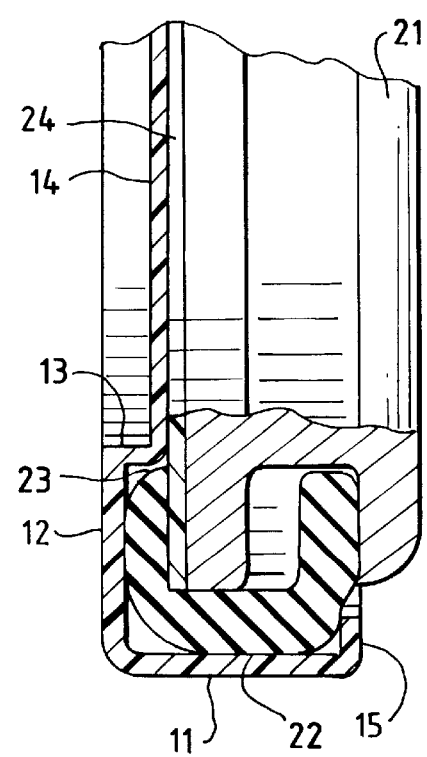
FIG. 6 shows a cross section of the cover diaphragm on the pickup of FIG. 4.

The form of the pickup outer edge 22 shown is the outer edge of an elastomeric retainer ring which is designed to hold a diaphragm 24 supplied with the stethoscope in place on the high frequency pickup. This supplied diaphragm 24 is shown in place in FIG. 4 and in FIG. 6. The supplied diaphragm is in place but not visible in FIG. 5. The function of the supplied diaphragm is to attenuate low frequency sounds so that high frequency sounds can be heard more clearly. When the cover diaphragm is used as shown in FIG. 2 and FIG. 3, then the disc of the cover diaphragm provides this function of attenuating the low frequency sounds. When the cover diaphragm is used with the supplied diaphragm 24 as shown in FIG. 5 and FIG. 6 then the disc of the cover diaphragm and the supplied diaphragm together attenuate low frequency sounds.

The inner band 13 is encircled by the outer band 11 which means that the cover diaphragm is recessed along the pickup inner edge away from the surface to be contacted when the stethoscope is used. This recess matches the recess of the diaphragm supplied with a stethoscope. It is important that there be no space to trap a layer of air between the disc 14 of the cover diaphragm and the supplied diaphragm 24 sufficient to abate the attenuating function when the cover diaphragm is used with the supplied diaphragm 24 as shown in FIG. 5 and FIG. 6.

Since the disc of the cover diaphragm can provide the attenuating function for the high frequency pickup no other diaphragm need be supplied with a stethoscope. The outer edge 22 and inner edge 23 of a high frequency pickup can be designed together with the outer band 11, the annulus 12, the inner band 13, and the disc 14 of the cover diaphragm in order to optimize the attenuation of low frequency sounds and to optimize the ease and reliability of attaching the cover over the pickup.

Using the cover diaphragm as the only diaphragm for a stethoscope high frequency pickup is preferred for several reasons. The acoustic properties can be optimized while isolating the pickup from pathogens. These acoustic properties will not change from one use to another use. Since in this case the cover diaphragm is the only diaphragm it can not be left off. Though it is true that in this case users can fail to replace used cover diaphragms and be no better off then when using a supplied diaphragm, it would be foolish to tempt the liability which would follow from failing to use a clean cover diaphragm with each patient.

Other equivalent forms for the outer edge 22 and inner edge 23 of a high frequency pickup and of the outer band 11, the annulus 12, the inner band 13, and the disc 14 of the cover diaphragm and other equivalent ways to attach the cover diaphragm over a stethoscope pickup will be obvious hereafter to persons skilled in the art. Therefore this invention is not limited to the particular examples shown and described here.

I claim:

1. In combination with a stethoscope, the stethoscope having a high frequency pickup, the pickup having a supplied diaphragm in the pickup, having an inner edge encircling the diaphragm, and having an outer edge encircling the inner edge, the supplied diaphragm being located at a diaphragm recess away from a surface contacted by the stethoscope when the stethoscope is used, a cover diaphragm, the cover diaphragm comprising:

an outer band encircling the pickup outer edge;

an annulus, the annulus being attached to the outer band and extending to just beyond the pickup inner edge;

an inner band, the inner band being attached to the annulus and the inner band being encircled by the outer band;

a disc, the disc being attached to the inner band, the disc being located at a disc recess away from the annulus, the disc recess matching the diaphragm recess, and the disc being the only element on the pickup which attenuates low frequency sounds when the supplied diaphragm is removed.

2. The device of claim 1 further comprising an ear protruding from the outer band toward the disc.

3. In combination with a stethoscope, the stethoscope having a high frequency pickup, the pickup having a supplied diaphragm in the pickup, having an inner edge encircling the diaphragm, and having an outer edge encircling the inner edge, the supplied diaphragm being located at a diaphragm recess away from a surface contacted by the stethoscope when the stethoscope is used, a cover diaphragm, the cover diaphragm comprising:

an outer band encircling the pickup outer edge;

an annulus, the annulus being attached to the outer band and extending to just beyond the pickup inner edge;

an inner band, the inner band being attached to the annulus and the inner band being encircled by the outer band;

a disc, the disc being attached to the inner band, the disc being located at a disc recess away from the annulus, the disc recess matching the diaphragm recess, and the disc and the supplied diaphragm attenuating low frequency sounds.

4. The device of claim 3 further comprising an ear protruding from the outer band toward the disc.

* * * * *